United States Patent [19]
Goodman et al.

[11] Patent Number: 5,919,797
[45] Date of Patent: Jul. 6, 1999

[54] HALOGENATED NAPHTHYL METHOXY PIPERIDINES FOR MAPPING SEROTONIN TRANSPORTER SITES

[75] Inventors: Mark M. Goodman, Atlanta; Bahjat Faraj, Lithonia, both of Ga.

[73] Assignee: Emory University, Atlanta, Ga.

[21] Appl. No.: 08/840,651

[22] Filed: Apr. 24, 1997

Related U.S. Application Data

[60] Provisional application No. 60/016,377, Apr. 26, 1996.

[51] Int. Cl.$^6$ .................. C07D 401/12; C07D 215/00; A61K 31/445
[52] U.S. Cl. .................. 514/319; 514/249; 514/307; 514/311; 514/320; 514/321; 514/322; 514/323; 514/324; 544/353; 546/139; 546/152; 546/196; 546/197; 546/198; 546/199; 546/201; 546/202; 546/205; 424/1.85; 424/1.89
[58] Field of Search .................. 544/353; 846/139, 846/152, 196, 197, 198, 199, 201, 202, 205; 514/249, 307, 311, 319, 320, 321, 322, 323, 324; 424/1.85, 1.89

[56] References Cited

U.S. PATENT DOCUMENTS

| | | | |
|---|---|---|---|
| 4,514,398 | 4/1985 | Regnier et al. | 514/245 |
| 4,529,730 | 7/1985 | Schneider et al. | 514/319 |
| 4,791,119 | 12/1988 | Langer | 514/317 |
| 5,169,855 | 12/1992 | Cain et al. | 514/319 |
| 5,296,479 | 3/1994 | Cain et al. | 514/256 |
| 5,317,024 | 5/1994 | Cain et al. | 514/317 |
| 5,372,813 | 12/1994 | Mathis, Jr. et al. | 424/1.85 |

FOREIGN PATENT DOCUMENTS

| | | |
|---|---|---|
| 5186561 | 3/1997 | Canada . |
| 2 514 353 | 9/1981 | France . |
| 95/22341 | 8/1995 | WIPO . |

OTHER PUBLICATIONS

Dhainaut et al. "Piperidinotriazinediamines" CA 100:68324, 1983.

Scatton et al. "SI. 81.0385: a novel selective and potent serotonin uptake inhibitor" CA 108:124383, 1988.

Connell et al. "Heterocyclic aryl, alkyl and cyclalkylacetic acid amide useful as antiatherosclerotics" CA 126:317323, 1997.

Wagner et al. "Principles of nuclear medicine" Sanders Co. pp. 166–177, 1995.

Biegon, A. et al. (1993), "[$^{125}$I]5–Iodo–6–nitroquipazine: a potent and selective ligand for the 5–hydroxytryptamine uptake complex. II. In vivo studies in rats," Brain Res. 619:236–246.

Hume, S.P. et al. (1991), "Citalopram: Labelling with Carbon–11 and Evaluation in Rat as a Potential Radioligand for In Vivo PET Studies of 5–HT Re–uptake Sites," Nucl. Med. Biol. 18(3):339–351.

Jagust, W.J. et al. (1993), "In vivo imaging of the 5–hydroxytryptamine reuptake site in primate brain using single photon emission computed tomography and [$^{125}$I] 5–iodo–6–nitroquipazine," Eur. J. Pharmacol. 242:189–193.

Kilbourn, M.R. et al. (1989), "Synthesis of Radiolabeled Inhibitors of Presynapti Monoamine Uptake Systems: [$^{18}$F]GBR 1311 (DA),[$^{11}$C]Nisoxetine (NE), and [$^{11}$C]Fluoxetine (5–HT)," J. Label Compound Radiopharm 26:412–414.

Mathis, C. et al. (1993), "Synthesis and Biological Evaluation of a PET Radioligand for Serotonin Uptake Sites: [pF–18]5–Fluoro–6–Nitroquipaine," J. Nucl. Med. 34:7P–8P.

Mathis, C.A. et al. (1994), "Synthesis of $^{123}$I, and $^{125}$I–Labelled 5–iodo–6–nitroquipazine," J. Labelled Compounds and Radiopharm. XXXIV(10):905–913.

Mulholland, G.K. et al. (1995), "Synthesis, In vivo Biodistribution and Dosimetry of [$^{11}$C]N–Methylpiperidyl Benzilate ([$^{11}$C]NMPB), a Muscarinic Acetylcholine Receptor Antagonist," Nucl. Med. Biol. 22(1):13–17.

Maryanoff, B.E. et al. (1987), "Pyrroloisoquinoline Antidepressants. 2. In–Depth Exploration of Structure–Activity Relationships," J. Med. Chem. 30:1433–1454.

Suehiro, M. et al. (1990), "In Vivo Labeling of the Dopamine D2 REceptor with N–$^{11}$C–Methyl–Benperidol," J. Nucl. Med. 31(12):2015–2021.

Suehiro, M. et al. (1991), "Radiosynthesis and Evaluation of N–(3–[$^{18}$F]Fluoropropyl)paroxetine as a Radiotracer for In Vivo Labeling of Serotonin Uptake Sites by PET," Nucl. Med. Biol. 18(7):791–796.

Suehiro, M. et al. (1993), "A PET Radiotracer for Studying Serotonin Uptake Sites: Carbon–11–McN–5652Z," J. Nucl. Med. 34(1):120–127.

*Primary Examiner*—Ceila Chang
*Attorney, Agent, or Firm*—Greenlee Winner and Sullivan PC

[57] ABSTRACT

Halogenated naphthyl methoxy piperidines having a strong affinity for the serotonin transporter are disclosed. Those compounds can be labeled with positron-emitting and/or gamma emitting halogen isotopes by a late step synthesis that maximizes the useable lifeterm of the label. The labeled compounds are useful for localizing serotonin transporter sites by positron emission tomography and/or single photon emission computed tomography.

15 Claims, No Drawings

HALOGENATED NAPHTHYL METHOXY PIPERIDINES FOR MAPPING SEROTONIN TRANSPORTER SITES

CROSS REFERENCE TO RELATED APPLICATIONS

This application is a continuation-in-part of United States Provisional Application No. 60/016,377, filed Apr. 24, 1996. +gi

ACKNOWLEDGEMENT OF FEDERAL RESEARCH SUPPORT

This invention was made, at least in part, with funding from the United States Department of Energy, Grant No. DE FG05-93 ER61737. Accordingly the United States Government may have certain rights in this invention.

BACKGROUND OF THE INVENTION

The ability of analog compounds to bind to localized ligands within the body would make it possible, in principle, to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, [$^{11}$C], has been used for PET, but its short half-life of 20.5 minutes limits its usefulness to compounds that can be synthesized and purified quickly, and to facilities that are proximate to a cyclotron where the precursor [$^{11}$C] starting material is generated. Other isotopes have even shorter half-lives. [$^{13}$N] has a half-life of 10 minutes and [$^{15}$O] has an even shorter half-life of 2 minutes. The emissions of both are more energetic than those of [$^{11}$C]. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope, [$^{18}$F], has a half-life of 110 minutes. This allows sufficient time for incorporation into a radio-labeled tracer, for purification and for administration into a human or animal subject. In addition, facilities more remote from a cyclotron, up to about a 200 mile radius, can make use of [$^{18}$F] labeled compounds. Disadvantages of [$^{18}$F] are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}$F-F. Reactions using $^{18}$F-F as starting material therefore yield products having only one half the radionuclide abundance of reactions utilizing K$^{18}$F as starting material. On the other hand, [$^8$F] can be prepared in curie quantities as fluoride ion for incorporation into a radiopharmaceutical compound in high specific activity, theoretically 1.7 Ci/nmol using carrier-free nucleophilic substitution reactions. The energy emission of [$^8$F] is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of [$^{18}$F] labeled compounds in PET has been limited to a few analog compounds. Most notably, [$^{18}$F]-fluorodeoxyglucose has been widely used in studies of glucose metabolism and localization of glucose uptake associated with brain activity. [$^8$F]-L-fluorodopa and other dopamine receptor analogs have also been used in mapping dopamine receptor distribution.

Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs.

Currently, there does not exist a single radiopharmaceutical that can be labeled with either fluorine-18, bromine-76 or iodine-123 amenable for regional distribution that is efficacious in differentiating major depression from other psychiatric disorders. Citalopram (Hume, S. P. et al., *Nucl. Med. Biol.* (1991) 18:339–351), paroxetine (Suehiro, M. et al., *Nucl. Med. Biol.* (1991) 18:791–796), fluoxetine (Kilbourn, M. R. et al., *J. Label Compound Radiopharm.* (1989) 26:412–414), and nitroquipazine (Mathis, C. et al.,*J. Nucl. Med.,* (1993) 34:7P–8P), potent serotonin transporter ligands, have been radiolabeled with carbon-11 and fluorine-18 as potential radiotracers for imaging and quantifying serotonin transporter sites in the brain using PET. Unfortunately, the in vivo affinity and selectivity for the serotonin transporter of these radiolabeled ligands did not reflect their in vitro potencies which resulted in poor quality images of brain regions rich in serotonergic neurons. Recently, a series of antidepressants, trans-1,2,3,5,6,10b-hexahydro-pyrrolo[2,1-a]isoquinoline derivatives have been found to be potent inhibitors with low and subnanomolar affinity for the serotonin transporter (Maryanoff, B. E. et al., *J. Med. Chem.* (1987) 30:1433–1454). The most potent inhibitor of the series, trans-1,2,3,5,6,10b-hexahydro-6-[4-(methylthio)phenyl]pyrrolo [2,1-a]isoquinoline (McN-5652Z) (Ki=0.68 nM vs. 100–200 nM [$^3$H]serotonin), has been labeled with carbon-11 as a PET radioligand for mapping serotonin transporter sites (Suehiro, M. et al., *J. Nucl. Med.* (1993) 31:841–848). Carbon-11 McN-5652Z showed the greatest accumulation in brain regions rich in serotonergic neurons with greater cortex to cerebellum ratios (4.3 to 1) than previously tested PET serotonin transporter ligands (Suehiro, M. et al., *J. Nucl. Med.* (1993) 34:120–127). However, the very short 20 minute half-life of carbon-11 minute half-life may not allow ample time for measuring the entry and longitudinal selective regional uptake of the radioligand and analysis of the presence of radiolabeled metabolites which is crucial in receptor imaging and tracer kinetic modeling. thus, there still exists a need for a greater than 20 minute half-life radiolabeled probe that demonstrates sub to low nanomolar affinity, high selectivity, and a low dissociation rate from the molecular serotonin transporter binding site. Because the serotonin transporter plays a pivotal role in serotonin neurotransmission, the development of radiopharmaceuticals radiolabeled with gamma emitting isotopes which exhibit pronounced brain uptake, very high selectivity and affinity for the transporter, and low non-specific binding would be excellent for the measurement of the density of presynaptic serotonin transporter sites by emission tomography.

French patent of addition 81/19025, (publication no: 2514353, Apr. 15, 1983) disclosed 4-(2-naphthylmethoxy)-piperidine, (NMP) as having anti-depressant activity. U.S. Pat. No. 4,791,119, Dec. 13, 1988, disclosed administering NMP as an appetite suppressant for treatment of obesity.

U.S. Pat. No. 5,169,855, Dec. 8, 1992, disclosed a series of N-substituted piperidine ethers including 4-[(halo-2-naphthalenyl) methoxy]-N-alkyl or aryl piperidines. In general, the described compounds were said to have pharmaceutical utility, agricultural utility or both. Pharmaceutical utility was said to be for treating physiological or drug induced psychosis or dyskinesia.

U.S. Pat. No. 5,296,479 discloses similar N-substituted piperidine ethers having a cycloalkyl group substituted on the piperidine nitrogen. The compounds appear to have sigma receptor binding activity and associated pharmacological effects, however, those compounds tested were poor dopamine receptor binders, compared with haloperidol.

U.S. Pat. No. 5,317,024 discloses other N-substituted piperidine ethers which also have sigma receptor binding activity but lack dopamine receptor binding activity when compared with haloperidol.

The 6-nitroquipazines have been disclosed as having high affinity for serotonin uptake sites in U.S. Pat. No. 5,372,813, Dec. 13, 1994. The possibility of halogen substitution was also disclosed. 6-nitroquipazines labeled with a radioactive halogen, specifically $^{125I\ I\ or\ 123}I$ were described by Mathis, C. et al., (1993) *J. Nucl. Med.* 34:7P–8P and Mathis, C. et al., (1994) *J. Label. Cmpds. Radiopharm.* 34:905–912. Other articles describing the binding, distribution in brain and in vivo SPECT imaging using a $^{123}I$ labeled 6-nitroquipazine have been described by Biegon, A. et al., (1993) *Brain Res.* 619:236–246 and by Jagust, W. J. et al., (1993) *Eur. J. Pharmacol.* 242:189–193.

Another substituted piperidine, 4-N-methylpiperidylbenzillate (NMPB) has been disclosed as being a muscarinic acetylcholine receptor antagonist (Mulholland, G. K. et al., (1995) *Nucl. Med. Biol.* 22:13–17). $^{11}C$-labeled NMPB was used for PET imaging of receptor distribution.

SUMMARY OF THE INVENTION

Halogenated naphthyl methoxy piperidines (HNMP) are provided, having unusually strong affinity for the serotonin transporter. Radiolabeled compounds of the invention, for example substituted with $^{18}F$, $^{75}Br$ or $^{123}I$, can be synthesized by a last step synthesis that maximizes the useable lifetime of the label. The incorporated label is stable to metabolism and in vivo loss of the radiohalogen. Radioactive isotopes of bromine, iodine or fluorine can be incorporated on several positions of the naphthalenyl group. Radiolabeled fluorine can be inserted on either the naphthalenyl group or the piperidine group. Consequently, a single radiopharmaceutical compound can be used for either positron emission tomography (PET) or single photon emission (SPECT) imaging. Compounds of the invention have the general structure

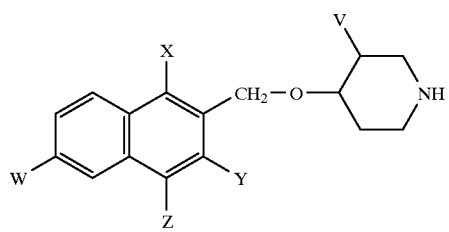

where W, X, Y and Z are independently H or halogen and V is H, F, $^{18}F(CH_2)_n{}^{18}F$, or $CH=CHI—CH=CH^{123}I$, $—CH—CH^{125}I$, $—CH—CHBr$, $—CH=CH^{xy}Br$ where xy is 75, 76, 77 or 82, and n is 0, 1 or 2.

Compounds of the invention have activity as specific ligands of the serotonin transporter. In particular, the 1-halonaphthalenyl pharmacophore has high affinity for the serotonin transporter. In vitro binding studies for the serotonin transporter were measured by testing inhibition of binding of [H-3] citalopram, a potent serotonin transporter ligand, to rat cortical homogenates. The concentrations of 4-[(1-halo-2-naphthalenyl) methoxy piperidines of the invention needed to achieve 50% inhibition of citalopram binding ($IC_{50}$) were as follows: bromo, 0.015 nM; chloro, 1.24 nM; fluoro, 3.37 nM; iodo, 4.1 nM. Halogen substituents can be in naturally-occurring or radioisotopic form.

Compounds of the invention are useful for emission tomography, especially so where the same chemical entity can be used for both positron emission tomography (PET) and for single photon emission computed tomography (SPECT). The high in vitro binding affinities for the serotonin transporter also provide pharmaceutical utility for the diagnosis, treatment or management of a variety of psychiatric, psychomoter and addictive disorders such as depression, obsessive-compulsive disorder, Parkinson's disease, Alzheimer's disease and alcohol abuse.

DETAILED DESCRIPTION OF THE INVENTION

Compounds of the invention provide substantially improved PET imaging for areas of the brain where information about distribution and density of serotonin transporter is desired. All the available positron-emitting isotopes which could be incorporated into a biologically-active compound have short half-lives. The practical utility of such labeled compounds is therefore dependent on how rapidly the labeled compound can be synthesized, the synthetic yield and the radiochemical purity of the final product. Even the shipping time from the isotope source, a cyclotron facility, to the hospital or laboratory where PET imaging is to take place, is limited. A rough calculation of the useful distance is about two miles per minute of half-life. Thus [$^{11}C$], with a half-life of 20.5 m is restricted to about a 40 mile radius from a source whereas compounds labeled with [$^{18}F$] can be used within about a 200 mile radius. Further requirements of an [$^{18}F$]-labeled compound are that it have the binding specificity for the receptor or target molecule it is intended to bind, that non-specific binding to other targets be sufficiently low to permit distinguishing between target and non-target binding, and that the label be stable under conditions of the test to avoid exchange with other substances in the test environment. More particularly, compounds of the invention must display adequate binding to the desired target while failing to bind to any comparable degree with other tissues or cells. Furthermore, the fluorine, iodine or bromine label must not be labile or unstable such that significant amounts appear in, e.g. bone or thyroid, or other non-target tissue, respectively.

Bromine-75 is a second attractive positron emission tomography (PET) radionuclide for radiolabeling because its 102 minute half-life also allows sufficient time (3×102 minutes) for incorporation into the radiopharmaceutical and for purification of the final product suitable for human administration. Secondly, Bromine-75 can be prepared in curie quantities as bromide ion for incorporation into the radiopharmaceutical in high specific activity by no-carrier added iododemetallation reactions. Finally the 102 minute half-life allows sufficient time for regional distribution up to a 200 mile radius from the manufacturing site. Other Br isotopes can be used, including $^{76}$Br, $^{77}$Br and $^{82}$Br.

A partial solution to the stringent requirements for PET imaging is to employ γ-emitting isotopes in SPECT imaging. [$^{123}$I] is a commonly used isotopic marker for SPECT, having a half-life of 13 hours for a useful range of over 1000 miles from the site of synthesis. Compounds of the invention can be rapidly and efficiently labeled with [$^{123}$I] for use in SPECT analysis as an alternative to PET imaging. Furthermore, because of the fact that the dihalogenated compounds of the invention can be labeled with either isotope, it is possible for the first time to compare the results obtained by PET and SPECT using the same tracer. Another useful iodine isotope is $^{125}$I.

The compounds of the invention therefore provide improved methods for imaging the serotoninergic transporter site in the brain using PET and SPECT. The methods entail administering to a subject (which can be human or animal, for experimental and/or diagnostic purposes) an image-generating amount of a compound of the invention, labeled with the appropriate isotope and then measuring the distribution of the compound by PET if [$^{18}$F] or other positron emitter is employed, or SPECT if [$^{123}$I] or other gamma emitter is employed. An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art without resort to undue experimentation.

It is understood that compounds of the invention can be labeled with an isotope of any atom or combination of atoms in the structure. While [$^{18}$F], $^{75}$Br, [$^{123}$I] and [$^{125}$I] have been emphasized herein as being particularly useful for PET, SPECT and tracer analysis, other uses are contemplated including those flowing from physiological or pharmacological properties of stable isotope homologs and is apparent to those skilled in the art.

EXAMPLE 1

Synthesis of 4-[(1-Bromo-2-naphthalenyl) methoxy] piperidine hydrochloride 1. Scheme 1 diagrams the reaction sequence.

1-Bromo-2-(bromomethyl)naphthalene 13:

A solution of 1-bromo-2-methyl naphthalene12 (5 g, 22.6 mmoles) and benzoyl peroxide (40 mg) in 75 ml of benzene was brought to vigorous reflux. A mixture of N-bromosuccinimide (NBS) (3.6 g, 20 mmoles) and benzoyl peroxide (40 mg) was added in small portions over a period of 20 minutes and refluxing continued for 1 hr. The reaction mixture was cooled and was quenched with saturated solution of NaHCO$_3$ and the benzene phase was washed twice with water, brine, dried over anhydrous magnesium sulfate and evaporated in vacuo to give a yellow semi-solid material which upon crystallization from hexane gave 4.1 g of 13 (60%). MP, 107–108° C. It showed a single spot on TLC (100% hexane, silica gel, R$_f$=0.60); NMR (CDCl$_3$) d 4.8 (s, 2H, CH$_2$—O), d 7.2–8.1 (m, 6H, naphthyl).

N-(tert-butoxycarbonyl)-4-hydroxypiperidine 14:

To a solution of 4-hydroxypiperidine (5 g, 50 mmoles) and triethyl amine in CH$_2$Cl$_2$ (100 ml) was added di-tert-butyl-dicarbonate (13.1 g, 60 mmoles) and the mixture was stirred for 24 hr. at 25° C. The reaction mixture was quenched with 50 ml of water and the CH$_2$Cl$_2$ solution was washed with saturated NaHCO$_3$, brine and then dried over anhydrous MgSO$_4$. The dried CH$_2$Cl$_2$ was evaporated under reduced pressure to give 10 g of 14 (85%).

4-[(1-Bromo-2-naphthalenyl) methoxy]-N-[tert-butoxycarbonyl]piperidine 15:

To a suspension of sodium hydride (60% oil dispersion, 1 g, 25 mmole) in anhydrous THF (50 ml) under argon was added a solution of 14 (2.01 g, 10 mmoles) in 15 ml of anydrous THF dropewise over a period of 10 min. The mixture was stirred at 25° C. for 25 min. This was then followed by the addition of 13 (3 g, 10 mmoles) dissolved in 15 ml of anhydrous THF. The reaction mixture was heated at 50–60° C. overnight. The reaction mixture was quenched with 50 ml of water and then extracted with 3×100 ml of ethyl ether. The ether fraction was washed with saturated solution of NaHCO$_3$, water, brine and was then dried over anhydrous MgSO$_4$. The anhydrous ether was evaporated in vacuo to give a yellow brown oil (2.7 g). The crude yellowish oil was purified by chromatography (silica, hexane/ethyl acetate, 90:10) to afford 1.2 g of 15 (44.4%) as a light creamy solid. A single component was detected by TLC (hexane/ethyl acetate, 90:10) R$_f$, 0.6; NMR (CDCl$_3$) d 1.5 (s, 9H, tBu), d1.6–2 (m, 4H, ring-CH$_2$), d 3.2 (m, 2H, ring-CH$_2$—N), d 3.6 ( m, 1H, , —CH—OH) d 3.8 (m, 2H, ring-CH$_2$—N—), d 4.8 (s, 2H, CH$_2$—O—), d 7.2–8.3 ( m, 5H, naphthyl). MS (HRFAB) calcd for C$_{21}$H$_{26}$BrNO$_3$(M$^+$) 420.1150 found 420.1153.

4-[(1-Bromo-2-naphthalenyl) methoxy]piperidine hydrochloride 1:

A solution of 15 (1.117 g, 2.65 mmole) in 4N HCl/dioxane (10 ml) was stirred at room temperature for 1 hr. The solvent was evaporated in vacuo to give a white precipitant which upon washing repeatedly with hexane gave 0.9 g of 1 (2.53 mmole) (95%). Anal (C$_{16}$H$_{19}$BrClNO) C,H,N. For chromatographic and spectral analysis, 0.7 g of 1 was dissolved in water (30 ml) and the solution was made basic with conc NH$_4$OH. The resulting oily precipitate was extracted with CH$_2$Cl$_2$ (3×50 ml). The CH$_2$Cl$_2$ fraction was washed with saturated NaHCO$_3$, H$_2$O, brine and dried over anhydrous MgSO$_4$. The dried CH$_2$Cl$_2$ solution was evaporated in vacuo to give 0.6 g of a light yellow oil that solidified upon standing as the free base form of 1. A single component was detected by TLC (hexane/ethyl acetate, 90:10) R$_f$, 0; (conc NH$_4$OH/methanol/hexane/ethyl acetate, 1:1:3:6) R$_f$, 0.35; NMR (CDCl$_3$) d 1.7–2.1 (m, 4H, CH$_2$-ring) d 2.8–3.2 (m, 4H, ring- (CH$_2$)$_2$—NH), d 3.7 (m, 1H, O—CH-ring), d 4.8 (2H, 5, CH$_2$—O—) d7.4–8.3 (m, 5H, naphthyl).

MS(HRFAB) calculated for C$_{16}$H$_{18}$(M$^+$+1) 320.0650 found 320.0657.

EXAMPLE 2

Synthesis of Compound 2: 4[(1-Iodo-2-naphthalenyl) methoxyl]piperidine hydrochloride. The reaction sequence is diagrammed in Scheme 2.

4-[(1-Iodo-2-naphthalenyl) methoxy]-N-[tert-butoxycarbonyl]piperidine) 16:

A solution of 15 (1 g, 2.4 mmole) in dry THF (50 ml) was cooled to −78° C. under argon. This was followed by the addition of 2.5 M solution of n-butyllithium in hexane (1.2 ml, 3.6 mmole) with a syringe through a rubber septum. The resulting mixture was stirred for 5 min. After the addition of a solution of $I_2$ in THF (1.2 g, 5 mmole), the mixture was stirred again at −78° C. for 30 min. and then at room temperature for 1 hr. The mixture was then added to 60 ml of water and extracted three times with 50 ml of methylene chloride. The combined methylene chloride extracts were washed with saturated solution of $NaHCO_3$, brine, and dried over anhydrous magnesium sulfate and the solvent was concentrated in vacuo to give 1.470 g of crude yellow oil. The crude oil was purified by column chromatography (silica, hexane/ethyl acetate, 90:10) to afford 1.07 g (60%) of 16 as a light yellow oil. A simple component was detected by TLC (hexane/ethyl acetate, 90:10) $R_f$, 0.6; NMR ($CDCl_3$) d1.5 (s, 9H, tBu), d1.6–1.9 (m, 4H, ring-$CH_2$), d 3.2 (m, 2H, ring-$CH_2$—NH) , d 3.7 (m, 1H, O—CH-ring), d 3.8 (m, 2H, ring-$CH_2$—NH), d 4.8 (s, 2H, —$CH_2$—O-ring), d 7.6–8.2 (m, 5H, naphthyl). MS (HRFAB) Calcd for $C_{21}H_{26}INO_3$ ($M^+$) 468.1036 found 468.1035.

4[(1-Iodo-2-naphthalenyl) methoxyl]piperidine hydrochloride 2: Following the procedure described for compound 1, compound 2 was obtained as a white crystalline powder.

EXAMPLE 3

Synthesis of compound 3: 4-[(1-Fluoro-2-naphthalenyl) methoxy]-piperidine hydrochloride. The reaction sequence is diagrammed in Scheme 3.

1-Fluoro-2-methyl naphthalene 17:

A solution of 1-bromo-2-methyl naphthalene 12 (1 g, 4.5 mmole) in dry THF (50 ml) was cooled to −78° C. under argon. This was followed by the addition of 2.5 M solution of n-butyllithium (2.4 ml, 6 mmole) and N-fluoro-dibenzene sulfonamide in THF (1.57 g, 5 mmole). The mixture was stirred at −78° C. for 10 min. and then at room temperature for 2 hr. The mixture was then added to 60 ml of $H_2O$ and extracted three times with 50 ml of methylene chloride. The methylene chloride fraction was washed with saturated solution of $NaHCO_3$, water, brine and dried over anhydrous magnesium sulfate. The solvent was then evaporated under reduced pressure to give 0.7 gram of a crude yellow oil. The crude oil was purified by chromatography (silica, 100% hexane) to afford 0.35 g of 17 (40%) as a colorless oil. A single component was detected by TLC (hexane) $R_f$, 0.634; NMR ($CDCl_3$) d 2.5 (s, 3H, —$CH_3$), d 7.3–8.1 (m, 6H, naphthyl).

1-Fluoro-2-(bromomethyl) naphthalene 18:

Following the procedure described for compound 13, compound 18 was obtained in 70% yield as a white solid.

4-[(1-Fluoro-2-naphthalenyl) methoxy]-N-[tert-butoxycarbonyl]piperidine 19:

Following the procedure described for compound 15, compound 19 was obtained in 50% yield. NMR($CDCl_3$) d 1.5 (m, 9H, tBu), d 1.6–1.9 (m, 4H, ring-$CH_2$), d 3.1 (m, 2H, ring-$CH_2$—N) d 3.6 (m, 11H, —O—CH-ring), d 3.8 (m, 2H, ring-$CH_2$—N—), d 4.8 (s, 2H, —CH—$_2$_O—), d 7.8–8.1 (m, 5H, naphthyl).

4-[(1-Fluoro-2-naphthalenyl) methoxy]-piperidine hydrochloride 3:

Following the procedure described for compound 1, compound 3 was obtained as a crystalline solid.

EXAMPLE 4

Synthesis of compound 4: 4-[(1-Chloro-2-naphthalenyl) methoxy]-piperidine hydrochloride. The sequence steps are shown in Scheme 4.

1-Trimethylstannyl-2-methyl naphthalene 20:

A solution of 1-bromo-2-methyl naphthalene 12 (2.5 g, 11.31 mmole) in dry THF (50 ml) was cooled to −78° C. under argon. This was followed by the addition of 2.5 M solution of n-butyllithium in hexane (6 ml, 15.3 mmole) with a syringe through a rubber septum. The resulting mixture was stirred for 5 min. After the addition of trimethylstannyl bromide (5.5 g, 22.5 mmole), the mixture was allowed to reach room temperature and then stirred for 1 hr. The mixture was added to 60 ml of water and extracted three times with 50 ml of methylene chloride. The methylene chloride fraction was washed with saturated solution of $NaHCO_3$, $H_2O$, brine and dried over anhydrous magnesium sulfate. The solvent was then removed in vacuo to give 3.9 g of a light yellow oil. The crude oil was purified by column chromatography (silica, 100% hexane) to afford 2.5 g of 20 (40%) as a colorless oil. A simple component was detected by TLC (hexane) $R_f$, 0.72; NMR ($CDCl_3$) d 0.6 [s, 9H, Sn(—$CH_3$)$_3$ ] d 2.7 (s, 3H, $CH_3$), d 7.2–8.0 (m, 6H, naphthyl).

1-Chloro-2-methyl naphthalene 21:

To the tin compound 20 (1 g, 3.3 mmole) in $CH_2Cl_2$ (50 ml) was added N-chlorosuccimimide NCIS (931 mg, 7 mmole). The mixture was stirred overnight. The mixture was washed with saturated solution of $NaHCO_3$, water, brine, dried with anhydrous magnesium sulfate, and concentrated in vacuo to yield 0.7 g of a crude yellowish semi-solid. The crude yellow semi-solid was purified by column chromatography (silica, 100% hexane) to afford 1.2 g of 21 (80%) as a white powder. A simple component was detected by TLC (100%) hexane) $R_f$, 0.69; NMR ($CDCl_3$) d 2.3 (3H, S, $CH_3$), d 7.2–8.2 (m, 6H, naphthyl).

1-Chloro-2-bromomethyl-naphthalene 22:

Following the procedure described for compound 13, compound 22 was obtained in 40% yielded. NMR ($CDCl_3$) d 4.8 (s, 2H, —$CH_2$) d 7.4–8.3 (m, 6H, naphthyl).

4-[(1-Chloro-2-naphthalenyl) methoxy]-N-[tert-butoxycarbony]piperidine) 23:

Following the procedure described for compound 15, compound 23 was obtained in 60% yield.

4-[(1-Chloro-2-naphthalenyl) methoxy]-piperidine hydrochloride 4:

Following the procedure described for compound 1, compound 4 was obtained as a white solid.

EXAMPLE 5

Synthesis of compound 5: 4-[(1-Bromo-3-iodo-2-naphthalenyl) methoxy]piperidine hydrochloride. The sequence steps are shown in Scheme 5.

1-Bromo-2-hydroxymethyl naphthalene 24:

Water (100 ml) and $CaCO_3$ (18 g, 180 mmole) were added to a solution of 13 in dioxane (100 ml) and the mixture was refluxed for 10 hr. The solution was cooled and the dioxane was removed under reduced pressure and the mixture was acidified with 1N HCl and extracted with methylene chloride. The combined methylene chloride fractions were washed with saturated solution of $NaHCO_3$, $H_2O$, brine, dried over anhydrous magnesium sulfate, and evaporated in vacuo to give a white solid which when crystallized from hexane afforded 7 g of 24 (84.3%). A single component was detected by TLC (100% hexane, $R_f$ 0; hexane/ethyl acetate 80:20, $R_f$, 0.5); NMR ($CDCl_3$) d 2.1 (m, 1H, H—O), d 5.0 (s, 2H, $CH_2$—OH), d 7.4–8.4 (m, 6H, naphthyl); MS (HRFAB) calcd for $C_{11}H_9BrO$ $(M+Li)^+$243.0003 found 243.0003.

1-Bromo-3-Iodo-2-hydroxymethyl naphthalene 25:

A suspension of thalium trifluoro acetate (1.37 g, 2.53 mmole) in anhydrous $CCl_4$ containing 24 (0.5 g, 2.1095 mmole) was refluxed under argon. Iodine (0.535 g, 2.1095 mmole) was added dropwise in a solution of $CCl_4$ (10 ml). The mixture was refluxed for another 60 min. The reaction was cooled and quenched with 10% solution of sodium thiosulfate and then extracted with 3×50 ml of methylene chloride. The combined methylene chloride fractions were thoroughly washed several times with $H_2O$, brine, dried with anhydrous magnesium sulfate, and evaporated in vacuo to give a dark brown thick oil. The crude dark brown oil was purified by chromatography (hexane/ ethyl acetate; 80:20) to afford 0.2 g of 25 (7%) as a light cream solid. A single component was detected by TLC (hexane/ethyl acetate; 80:20) $R_f$, 0.5; NMR ($CDCl_3$). $\delta$4.8–5 (2H, d, $CH_2$—OH), d 7.4–8.4 (m, 5H, naphthyl). MS (HRFAB) (M+Li)$^+$ calcd for $C_{11}H_8OBrI$, 368.8963 found 368.8978.

1-Bromo-3-Iodo-2-chloromethyl naphthalene 26:

A solution of 25 (206 mg, 0.60 mmole) in carbon tetrachloride (2 ml) containing triphenylphosphine (393 mg, 1.5 mmole) was heated under reflux for 3 hr. The reaction mixture was washed with water, brine, dried with anhydrous $MgSO_4$ and evaporated in vacuo to give a dark yellow semi-solid. The yellow semi-solid was purified by column chromatography (100% hexane) to afford 80 mg. of 26 (40%) as a white powder (40%). A single component was detected by TLC (100% hexane) $R_f$, 0.64.

4-[(bromo-3-iodo-2-naphthalenyl) methoxy]-N-[tert-butoxycarbonyl]piperidine 27:

Following the procedure described for compound 15, compound 27 was obtained in 8.4% yield. NMR ($CDCl_3$) d 1.5 (s, 9H, t-butyl), d 1.7–1.9 (m, 2H, ring-$CH_2$—), d 3.8 (m, 3H, —O—CH— and ring-$CH_2$—N—), d 5.1 (s, 2H, $CH_2$—O-ring), d 7.4–8.4 (m, 5H, naphthyl).

4-[(1-Bromo-3-iodo-2-naphthalenyl) methoxy]piperidine hydrochloride 5:

Following the procedure described for compound 1, compound 5 was obtained as a yellow solid.

EXAMPLE 6

Synthesis of compound 6: 4-[(1-bromo-4-iodo-2-naphthalenyl) methoxy]piperidine hydrochloride. The sequence steps are shown in Scheme 6.

1-Bromo-2-acetyl-methyl naphthalene 28:

A mixture of 24 (2.5 g, 10.5 mmole), acetic anhydride (5.1 g, 50 mmole), pyridine (3.9 g, 50 mmole) and methylene chloride (50 ml) was stirred at 25° C. for 12 hr. The methylene chloride was washed with saturated solution $Na_2CO_3$, 4N HCl, $H_2O$, brine, dried with anhydrous magnesium sulfate and evaporated in vacuo to afford 3 g of 28 as a light yellow oil. A single component was detected by TLC (silica hexane/ethyl acetate; 90:10) $R_f$, 0.70; NMR ($CDCl_3$) d 2.2 (s, 3H, —$CH_3$), d 5.4 (s, 2H, —CH2—O—), d 7.4–8.3 ( m, 6H, naphthyl).

1-Bromo-4-iodo-2- acetyl methyl naphthalene 29:

Following the procedure described for compound 25, compound 29 was obtained in 10% yield. NMR ($CDCl_3$) d 2.2 (s, 3H, —$CH_3$) d 5.4 (s, 2H, —$CH_2$—O—), d 7.4–8.4 (m, 5H, naphthyl). MS (HRFAB) (M+Li)$^+$ calcd for $C_{13}H_{10}BrIO_2$ (410.9069), observed (410.9058).

1-Bromo-4-Iodo-2-hydroxymethyl-naphthalene 30:

To a solution of 29 (50 mg) in methanol (5 ml) was added 1 ml solution of $K_2CO_3$ and the mixture was stirred for 2 hr. at room temperature. The methanol was removed in vacuo and the residue was extracted with methylene chloride (2×50 ml). The methylene chloride fraction was washed with 1N HCl, $H_2O$, brine, dried with anhydrous $MgSO_4$ and evaporated in vacuo to give 40 mg of 30 (90%) as white crystalline solid which upon TLC analysis (silica, hexane/ethyl acetate, 90:10) showed a single component $R_f$, 0.4.

1-Bromo-4-Iodo-2-Chloromethyl Naphthalene 31:

Following the procedure described for compound 26, compound 31 was obtained in 70% yield.

4-[1-bromo-4-iodo-2-naphthalenyl) methoxy]-N-[tert-butoxycarbonyl]piperidine 32:

Following the procedure described for compound 15, compound 32 was made in 25% yield. NMR ($CDCl_3$) d 1.5 (s, 9H, t-Butyl), d 1.8–2.0 (m, 4H—$CH_2$-ring), d 3.1 (m, 1H, O—CH-ring), d 3.8 (m, 2H, CH2—N-ring), d 4.8 (s, 2H, —CH2—O—), d 7.2–8.4 (m, 5H, naphthyl).

4-[( 1-bromo4- iodo-2-naphthalenyl) methoxy]piperidine hydrochloride 6:

Following the procedure described for compound 1, compound 6 was obtained as a white solid.

EXAMPLE 7

Synthesis of compound 7: 4-[(1-Bromo-6-iodo-2-naphthalenyl) methoxy]piperidine hydrochloride. The sequence of reaction steps is shown in Scheme 7.

1.6-Dibromo-2-methyl naphthalene 33 and 1,6-dibromo-2-bromomethyl naphthalene 34:

Bromine in glacial acetic acid (2.256 g, 14.1 mmole) was added dropwise to a solution of 12 (1 g, 7.042 mmole) in glacial acetic acid over a period of 40 min at 25° C. The solution was then heated at 70° C. for 1 hr. The reaction mixture was added to 50 ml of water and extracted several times with $CH_2Cl_2$. The combined $CH_2Cl_2$ extracts were thoroughly washed with saturated solution $NaHCO_3$, $H_2O$, brine, dried with anhydrous $MgSO_4$, and concentrated in vacuo to yield 1.5 g of a yellow oil. This was purified by column chromatography (silica, 100% hexane) to afford two fractions that were separable. The first fraction consisted of a single component (TLC for the first fraction; 100% hexane; $R_f$, 0.70); NMR ($CDCl_3$) d 2.6 (s, 3H, —$CH_3$), d 7.2–8.4 (m, 5H, naphthyl). The second fraction consisted of a single component (TLC for the second fraction, 100% hexane; $R_f$, 0.514; NMR ($CDCl_3$) d 4.8 (s, —$CH_2$), d 7.2–8.4 (m, 5H, naphthyl). Chromatographic analysis and NMR spectrum suggested that the first fraction is compound 33 and the second fraction is compound 34.

4-[(1.6-Dibromo-2-naphthalenyl) methoxy]-N-[tert-butoxycarbonyl]piperidine) 35:

Following the procedure described for 15, compound 35 was obtained in (70%) yield .NMR ($CDCl_3$) d 1.8 (s, 9H, t-butyl), d 1.8–2 (m, 4H, $CH_2$-ring), d 3.2 (2H, m, —$CH_2$—N-ring), d 3.6 (m, 1H—O—C-ring), d 3.8 (M, 2H, —$CH_2$—N—C-ring), d 4.8 (s, 2H, —$CH_2$—0), d 7.4–8.4 (m, 5H, naphthyl).

4-[(1-Bromo-6-tributyl stannyl-2-naphthalenyl) methoxy]-N-[tert-butoxycarbonyl]piperidine 36:

To a solution of compound 35 (250 mg, 0.5 mmole) in anhydrous toluene (10 ml) under argon was added hexabutyl tin (348 mg, 0.6 mmole), tetrakis (triphenyl phosphine) (0) (2.6 mg, 0.0023 mmole) palladium acetate II (13 mg, 0.057 mmole) and the mixture was heated under reflux for 24 hr. Water was added to the mixture and extracted with 3×50 ml of methylene chloride. The combined methylene chloride was washed with saturated $NaHCO_3$, $H_2O$, brine, dried with anhydrous magnesium sulfate, and evaporated in vacuo to give 250 mg of a crude brown oil. The crude brown oil was purified by column chromatography (silica gel hexane/ethyl acetate; 97:3) to afford 75 mg of 36 (35%) as a colorless viscous oil. A single component was detected by TLC (hexane: ethyl acetate 95/S,) $R_f$, 0.55; NMR ($CDCl_3$) d 1.8 (m, 36H), d 1.8–2 (m, 4H, $CH_2$-ring) d 3.2 (m, 2H, ring-$CH_2$—N—) d 3.6 (m, 1H, —O—CH-ring), d 4.8 (s, 2H, —$CH_2$—0), d 7.2–8.3 (m, 5H, naphthyl).

4-[(1-Bromo-6-iodo-2-naphthalenyl)-methoxyl-N-[tert-butoxy carbonyl]piperidine 37:

A solution of 36 (180 mg, 0.254 mmole) and iodine (645 mg, 2.54 mmole) in methylene chloride (50 ml) was stirred at room temperature overnight. The reaction mixture was added to 10% sodium thiosulfate (50 ml). The methylene chloride fraction was washed with saturated $NaHCO_3$, $H_2O$, brine, dried with anhydrous magnesium sulfate and evaporated in vacuo to give a yellow semisolid. The crude product was purified by column chromatography (silica, hexane/ethyl acetate; 80:20) to afford 60 mg of 37 (30%) as a light yellow oil. A single component was detected by TLC (hexane/ethyl acetate; 90:10) $R_f$, 0.54; NMR ($CDCl_3$) d 1.5 (s, 9H, t-butyl), d 1.6–1.9 (m, 4H, —$CH_2$-ring), d 3.2 (m, 2H, —$CH_2$—NH-ring), d 3.6 (M, 1H, —O—CH-ring), d 3.8 (m, 2H—$CH_2$—NH-ring), d 4.8 (s, 2H, —$CH_2$—O-ring), d 7.4–8.4 (m, 5H, naphthyl).

4-[(1-Bromo-6-iodo-2-naphthalenyl) methoxyl piperidine hydrochloride 7:

Following the procedure described for compound 1, compound 7 was obtained as a white solid.

EXAMPLE 8

Synthesis of compound 8: 4-[(1-Bromo-2-naphthalenyl) methoxy]-3-fluoro-piperidine hydrochloride. The sequence of reaction steps is shown in Scheme 8.

1Benzoyl-1,2,3,6-tetrahydropyridine 39:

Benzoyl chloride (60 mmole) is added to a solution of 38 (60 mmole) in pyridine at 4 C. The mixture is allowed to stir for about 1–2 hrs and then further stirred at room temp for 12 hrs. The reaction mixture is made acidic and then extracted with methylene chloride. Following work-up and flash chromatography affords 39.

3,4-Epoxy-N-benzoyl piperidine 40:

A solution of metachloroperbenzoic acid (12 mmole) in methylene chloride is added dropwise to a solution of 39 at 4 C. The reaction mixture is allowed to stir overnight at room temperature. It is made basic and then extracted with methylene chloride. Following work-up and flash chromatography affords 40.

1-Benzoyl-3-fluoro-4-hydroxy piperidine 41:

A mixture of 40 (5 mmole), $KHF_2$ (22 mmole) in ethylene glycol is heated at 160° C. for about 5–7 hrs. Sodium carbonate solution is added to the reaction and then is extracted with methylene chloride. Following work-up and flash chromatography affords 41.

4-[(1-Bromo-2-naphthalenyl) methoxy]-3-fluoro-N-benzoyl piperidine 42:

Compound 42 is prepared according to the procedure described for compound 15.

4-[(1-Bromo-2-naphthalenyl) methoxy]-3-fluoro-piperidine hydrochloride 8:

The benzamide is cleaved as a result of the treatment of 42 with sodium in methanol at room temperature for about one hour. Following work-up and flash chromatography affords 8.

EXAMPLE 9

Synthesis of compound 9: 4-[(1-Bromo-2-naphthalenyl) methoxy]-3-fluoromethyl piperidine. The sequence of reaction steps is shown in Scheme 9.

1-Benzoyl-2-carbomethoxy-piperidone 44:

To a suspension of sodium hydride (25 mmole) and sodium dimethyl carbonate (25 mmole) in anhydrous THF under an atmosphere of argon, is added a solution of 43 (25 mmole) in THF dropwise over a period of 30 min. The mixture is allowed to stir at 50° C. overnight. Following work-up and flash chromatography affords 44.

1-Benzoyl-3-hydroxymethyl-4-hydroxy piperidine 45:

A suspension of lithium aluminum hydride (25 mmole) in anhydrous ether under argon is refluxed until most of the hydride is dissolved. A solution of 44 in ether is added slowly. The reaction mixture continues refluxing for an additional 30 min. Any excess LAH is decomposed by the addition of ethyl acetate and 6N HCl. The aqueous layer is then made basic with 3N NaOH and the mixture is extracted repeatedly with ether. Standard work-up and flash chromatography affords 45.

1-Benzoyl-3-methyl tosylate-4-hydroxy piperidine 46:

To a solution of 45 (7 mmole) in anhydrous pyridine at 4° C., is added para-toluenesulfonyl chloride (7.0 mmole). The mixture is stirred in ice-water for one hour. It is then acidified with 1N HCl and extracted repeatedly with methylene chloride. Standard work-up and flash chromatography affords 46.

1-Benzoyl-2-fluoromethyl-hydroxy piperidine 47:

A solution of 46 (10 mmole) and tetrabutylammonium fluoride (1M solution) in THF is heated under reflux for 1 hr. Standard work-up and flash chromatography affords 47.

4-[(1-Bromo-2-naphthalenyl) methoxy]-3-fluoromethyl-1-benzoyl piperidine 48:

Compound 48 is synthesised according to the procedure described for compound 15.

EXAMPLE 10

Synthesis of compound 10: 4-[(1-Bromo-2-naphthalenyl) methoxy]-3-(fluoroethyl) piperidine. The sequence of reaction steps is shown in Scheme 10.

4-[(1-Bromo-2-naphthalenyl) methoxy]-3-fluoromethyl piperidine 9:

Compound 9 is prepared according to the procedure described for compound 8.

1-Benzoyl-3-(ethyl acetate)-4-piperdone 49:

Compound 49 is prepared according to the procedure described for compound 44.

1-Benzoyl-3-hydroxyethyl-4-hydroxy piperidine 50:

Compound 50 is prepared according to the procedure described for compound 45

1-Benzoyl-3-(1-tosyl ethane)-4-hydroxy piperidine 51:

Compound 51 is prepared according to the procedure described for compound 46.

1-Benzoyl-3-(fluoroethyl)-hydroxy-piperidine 52:

Compound 52 is prepared according to the procedure described for compound 47.

4-[(1-Bromo-2-naphthalenyl) methoxy]-3-(fluoroethyl)-1-benzoyl piperdine 53:

Compound 53 is prepared according to the procedure described for compound 15.

4-[(1-Bromo-2-naphthalenyl) methoxy]-3-(fluoroethyl) piperidine 10:

Compound 10 is prepared according to the procedure described for compound 8.

EXAMPLE 11

Synthesis of compound 11: 4-[(1-Bromo-2-naphthalenyl) methoxy]-3-(E-1-iodoethylene)-piperidine. The sequence of reaction steps in shown in Scheme 11.

1-Benzoyl-3-ethynyl-4-hydroxy piperidine 54:

To a solution of ethynyl magnesium chloride in THF (5 mmole) at 0° C., is added dropwise a solution of 40 (5.8 mmole) in THF. The mixture is allowed to stir at 0–10° C. for 1 hour, then at room temperature for an additional hour and then heated with gentle reflux for 30 mm. The reaction mixture is added to ice-water and the formed precipitate, $Mg(OH)_2$, is dissolved in 30% $H_2SO_4$. The product formed is extracted repeatedly with methylene chloride. Standard work-up and flash chromatography affords 54.

1-Benzoyl-3-(1-tributylstannyl ethylene)-4-hydroxy piperidine 55:

Compound 54 (5mmole), tributyltin hydride (5.1 mmole), and azobisisobutyronitrile (10 mg) is refluxed in toluene under argon for 6 hr. Standard work-up and flash chromatography affords 55.

1-Benzoyl-3- [(E)-1-iodoethylene]-4-hydroxy piperidine 56:

The stannyl compound 55 (4 mmole) is suspended in $CCl_4$ and the resulting mixture is cooled to 0° C. and stirred under red lights. Iodine monochloride (4 mmole) is added and the resulting solution is removed from the ice bath and stirring continued until colorless solution results. Standard work-up and flash chromatography affords 56.

4-[(1-Bromo-2-naphthalenyl) methoxy]-3-(E-1-iodoethylene)-N-benzoyl piperidine 57:

Compound 57 is prepared according to the procedure described for compound 15.

4-[(1-Bromo-2-naphthalenyl) methoxyl-3-(E-1-iodoethylene)-piperidine 11:

Compound 11 is prepared according to the procedure described for compound 8.

EXAMPLE 12

Synthesis of compound 70: 4-[(2-quinolenyl) methoxy] piperdine hydrochloride. The sequence of reaction steps is shown in Scheme 15. Related compounds according to Scheme 15 are also described.

2-Bromomethylquinoline 81:

Following the procedure described for compound 13, compound 81 was obtained in 40% yield.

(4[(2-quinolenyl) methoxy]N-[tert-butoxycarbonyl]) piperidine 82:

Following the procedure described for compound 15, compound 82 was obtained in 70% yield.

4-[(2-quinolenyl) methoxy]piperdine hydrochloride 70:

Following the procedure described for compound 1, compound 70 was obtained as lightly pinkish crystalline solid.

A similar synthetic pathway is followed for the formation of isoquinolenyl-71, quinoxalenyl-72, indolenyl-73, benzimidazolenyl-74, benzothiozolenyl-75, benzoxazolenyl-76, benzofuranlenyl-17, benzothiophenyl-78, and benztriazoleny-methoxy piperidine 79.

EXAMPLE 13 (See Scheme 12)

Radiolabelled Synthesis

4-[(1-Tributylstannyl-2-naphthalenyl) methoxy] piperidine 64:

A solution of 1 (0.5 g, 1.6 mmole) in dry THF (50 ml) was cooled to −70° C. under argon. This was followed by the addition of 2.5 M solution of n-butylithiumin hexane (0.8 ml, 2.1 mmole) and tributyltin chloride (1.7 g, 5 mmole) and the reaction mixture was stirred for 30 min at −70° C. and then for 1 hr at room temperature. The rations mixture was then added to 50 ml of water and extracted with methylene chloride. The methylene chloride fractions were washed with saturated solution of $NaHCO_3$, $H_2O$, brine, dried with anhydrous $MgSO_4$ and evaporated in vacuo to give 64 as light semi-solid. A single component was detected by TLC (ammonium hydroxide/methanol/ethyl acetate/hexane; 1:1:8:2) $R_f$, 0.5; NMR ($CDCl_3$) d 0.8–1.5 (m, 27H, 3× n-butyl); d 4.6 (s, —CH—O-ring); d 7.8–8.0 (m, 6H, naphthyl).

4-[(1-123-Iodo-2-nathalenyl) methoxyl piperidine 58:

Aqueous $H_2O_2$ (50 ml, 3% w/v) was added to a solution of compound 64 (1 mg), 0.1N HCl, 123-I-sodium iodide (12.2 mCi), and ethanol (500 ml). The reaction was allowed to proceed for 30 min and was then terminated by the addition of 0.1 ml solution of sodium thiosulfate (300 mg/ml). The reaction mixture was neutralized by the addition of saturated solution of $NaHCO_3$ and then extracted with ethyl acetate (1×1.0 ml). The combined ethyl acetate fractions were dried by passing through anhydrous $Na_2SO_4$ column and evaporated to dryness in vacuo. The residue was dissolved in 250 ml of methanol and passed through an activated SEP-PAC cartridge (C18) and eluted with a solution made up of 75% methanol/25% water/0.25% triethylamine. Fractions of 2 ml were collected and counted. Radiochromatographic analysis showed that greater than 90% of the activity was associated with the $R_f$ corresponding with that of 2.

Biodistribution studies in rats showed that the administration of 58 did not lead to selective accumulation of the radioactivity in serotonergic neurons.

4-[(1-76-Bromo-2-naphthalenyl) methoxy]piperidine 59:

The radiolabelling of 59 is accomplished by electrophilic substitution from the corresponding tributylstannyl derivative 64 with bromine −76. To a vial containing [76-bromine] $NH_4$ in 200 ml of water, are added 500 mg of 59 and 50 ml of 3% $H_2O_2$ solution. The labelling process is stopped 30 min later by the addition of 1 mg of sodium sulfite. The reaction mixture is neutralized by the addition of saturated solution of sodium bicarbonate and then extracted with ethyl acetate. The ethyl acetate fractions are dried by passing through anhydrous sodium sulfate column and then evaporated in vacuo. The purification of the radioactivity from the reaction is carried out by using a SEP-PAC (C18) column and elution with methanol/water/ triethylamine (75:25:0.25). Radiochemical purity is assessed by radio-TLC. In rats, biodistribution kinetics can confirm whether preferential uptake of 59 occurs in brain regions rich in serotonergic innervations such as the frontal cortex, and hypothalamus.

EXAMPLE 14

Synthesis of compounds 60–63: (Scheme 13)

1-Benzoyl-3-acetate-4-hydroxypiperidine 65:

A mixture of 40 and sodium acetate in ethylene glycol is heated at 16° C. for about 5–7 min. Sodium bicarbonate is added to the reaction mixture and then extracted with $CH_2Cl_2$. Following work-up and flash chromatography affords 65.

4-[(1-Bromo-2-naphthalenyl) methoxy]-3-acetate-N-benzoyl piperidine 66:

Compound 66 is prepared according to the procedure described for compound 15.

4-[(1-Bromo-2-naphthalenyl) methoxy]-3-hydroxy-N-benzoyl-piperidine 67:

Compound 67 is prepared according to the procedure described for compound 30.

4-[(1-Bromo-2-naphthalenyl) methoxy]-3 (methanesulfonyloxy)-N-benzoyl piperidine 68:

A solution of the alcohol 67 (1 mmole) in THF is cooled to 0° C. Methanesulfonyl chloride (1 mmole) and triethylamine (1 mmole) are added and the solution is stirred at 0° C. for 6 hr. Standard work-up and flash chromatography affords 68.

4-[(1-Bromo-2-nathalenyl)-methoxy]-3-$^{18}$F-fluoro-piperidine 60:

[$^{18}$F]-Fluoride was produced from a Seimens cyclotron using $^{18}$O (p,n)$^{18}$F reaction with 11 MeV protons on 95% enriched [$^{18}$O] water. After evaporation of the water and drying of the fluoride by acetonitrile evaporation, compound 68 is introduced in an acetonitrile solution (1.0 ml). The no carrier added fluorination reaction is carried out at 85° C. for 30 min. in a sealed vessel in the presence of potassium carbonate and Kryptofix (Aldrich Chemical Company). Unreacted $^{18}$F$^-$ is removed by diluting the reaction mixture with $CH_2Cl_2$ followed by passage through silica gel Sep-Pak. The methylene chloride is evaporated to dryness and deprotected by treating it with Na/methanol. Purification and isolation of the desired product 60 is accomplished by HPLC chromatography.

4-[(1-Bromo-2-naphthalenyl)-methoxy]-3-$^{18}$F-fluoromethyl-piperidine and 61 and 4-[(1-bromo-2-naphthalenyl)-methoxy]-3-$^{18}$F-fluoroethyl piperidine 62:

Compound 61 and compound 62 are prepared and purified according to the procedure described for the radiolabelling of compound 60. This occurs as a result of the nucleophilic displacement of the respective tosylates 46 and 51 with the cyclotron produced $^{18}$F.

EXAMPLE 15

Preparation of compound 63: (See Scheme 14)

4-[(1-Bromo-2-naphthalenyl)-methoxy]-3-(tributylstannylethylene)-piperidine 69:

Compound 69 is prepared by the reaction of 11 with n-butyllithium and tributyltin chloride according to the procedure described for 64.

4-[(1-Bromo-2-naphthalenyl)-methoxy -3-(E$^{123}$I-1-iodoethylene) piperidine 63:

Compound 63 is prepared according to the procedure described for compound 58.

BIOLOGICAL ACTIVITY

Many compounds have been described in the literature as selective inhibitors of the presynaptic reuptake of serotonin (5-hydroxytryptamine,5-HT). A number of them including fluoxetine, fluvoxamine, paroxitine and citalopram, have been studied in humans. Clinical studies have suggested that these compounds possess considerable therapeutic value in the treatment of depression, and several other disorders including obsessive-compulsive disorders, eating disorders, alcoholism and drug addiction. A good correlation exists between the capacities of a variety of drugs to inhibit [$^3$-H]-citalopram binding and [$^3$-H]-5HT uptake in rat cortex, thus allowing this binding test to be used in screening for new 5-HT uptake inhibitors.

Table 1 describes a series of naphthalenylmethoxy piperidine derivatives of the invention exhibiting 5-HT uptake inhibitory activity. The affinity of these compounds for neuronal 5-HT uptake transporter complex was tested in competitive radioligand binding assay using 3-H-citalopram, a very potent inhibitor of 5-HT uptake in the brain.

The results of this study showed that among the seven halogenated naphthalenyl methoxy piperidine compounds tested, the bromo-derivative 1 was the most potent inhibitor of [$^3$-H]-citalopram binding to rat cortical tissue preparation. It was 100-fold more potent than fluoxetine (Prozac). The chloro-4, fluoro-3, and iodo-2, compounds showed inhibitory activity comparable to that of fluoxetine and fluvoxamine. The replacement of either of the hydrogen at positions 3, 4 or 6 with an iodine of compound 1, resulted in substantial loss in activity (Table 1). Substitution of the naphthyl ring with a heterocyclic one resulted in a reversal of pharmacological potency. 2-Quinolenyl-methoxy-piperidine 70 was devoid of affinity for the serotonin transporter, but displayed a high selectivity as an antagonist of 5-HT$_3$ function. This demonstrated the importance of the aromatic ring in modulation of serotonergic neurotransmission among these compounds. The inhibitory effect can have significant therapeutic values in a number of neuropsychiatric disorders, Alzheimer's disease and prostate cancer.

TABLE 1

| Compound | [$^3$H]-Citalopram Binding (NM) | |
|---|---|---|
| | IC$_{50}$ | Ki |
| 1 | 0.02 | 0.014 |
| 2 | 5.9 | 4.13 |
| 3 | 5.74 | 3.37 |
| 4 | 2.12 | 1.24 |
| 5 | 54.6 | 36.9 |
| 6 | 24.6 | 16.7 |
| 7 | 60.0 | 58.4 |
| 70* | >100 | >100 |

*4-[(2-quinolenyl)-methoxy] piperidine 70 was a potent inhibitor of 5-HT$_3$ receptor activity. It blocked the binding of [3H] GR65630 to serotonergic synaptosomal preparation with an IC50 of 7.4 nM and a Ki of 3.24 nM.

Scheme 1

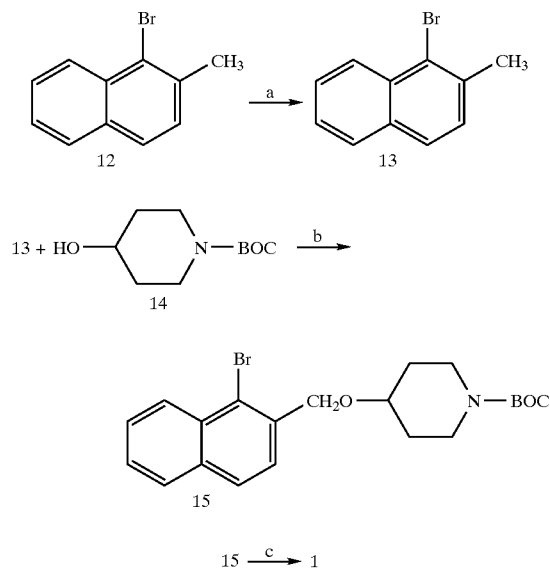

Reagents (a) NBS; (b) NaH, THF; (c) HCl/dioxane

Scheme 2

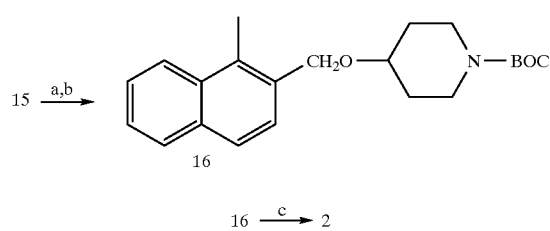

Reagents (a) nBuLi/THF; -70 C; (b) I$_2$/THF; (c) HCl/dioxane

Scheme 3
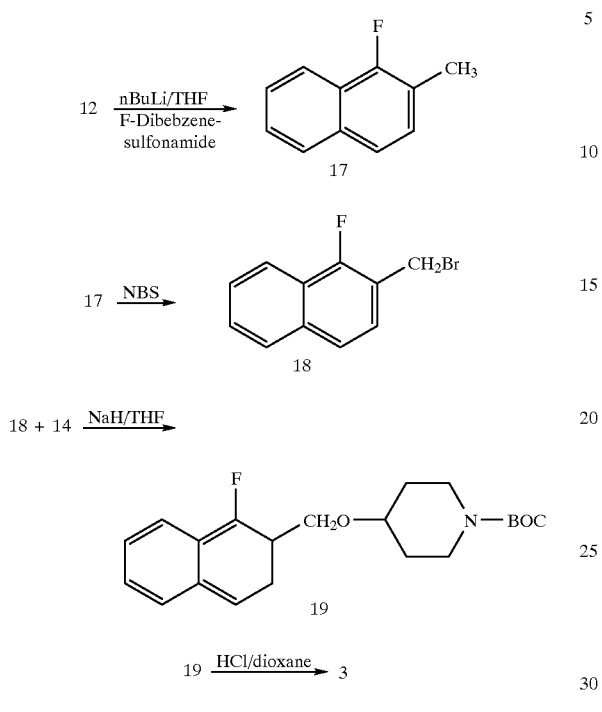
Scheme 4
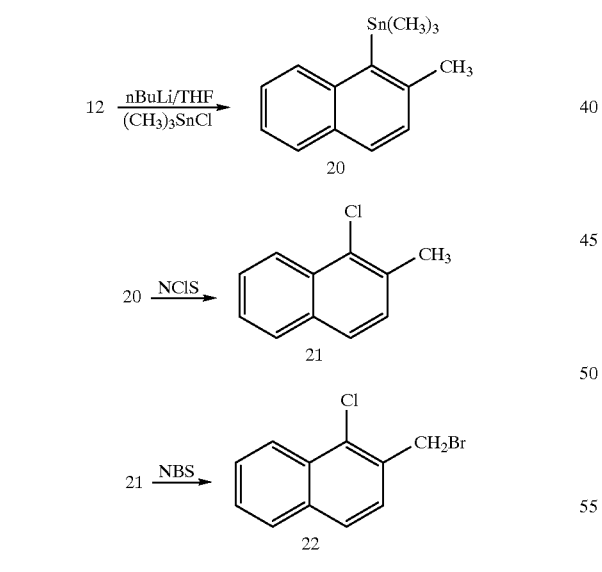
23 $\xrightarrow{\text{HCl/dioxane}}$ 4
Scheme 5
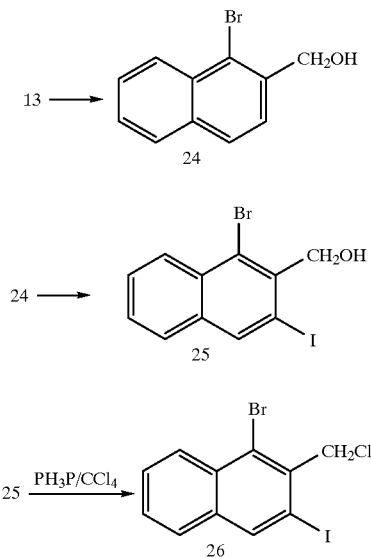
26 + 14 $\xrightarrow{\text{NaH/THF}}$
27 $\xrightarrow{\text{HCl/dioxane}}$ 5
Scheme 6
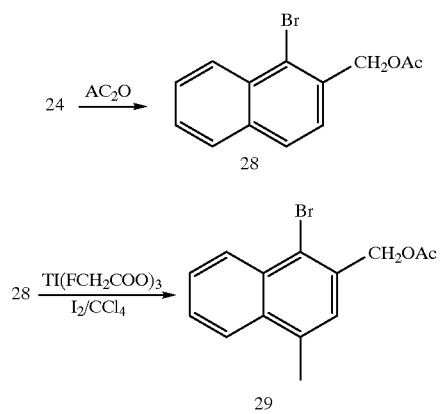

19
-continued
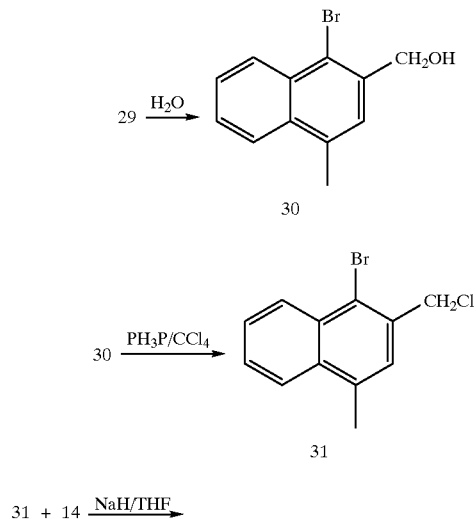
20
-continued
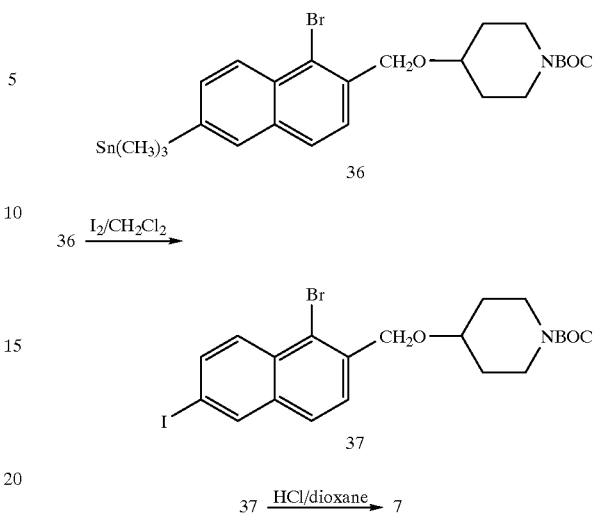
Scheme 7
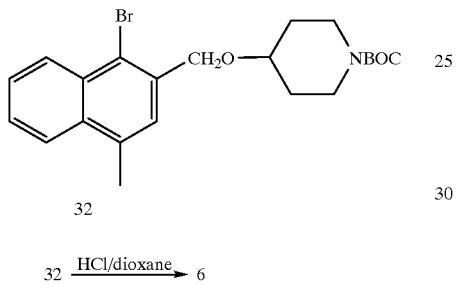
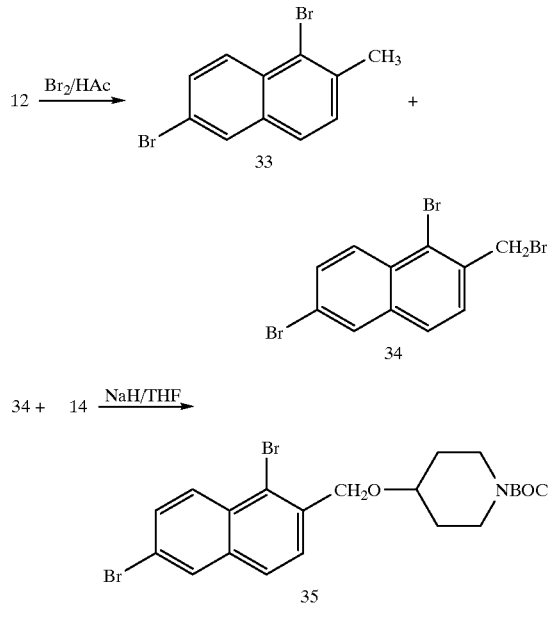
Scheme 8
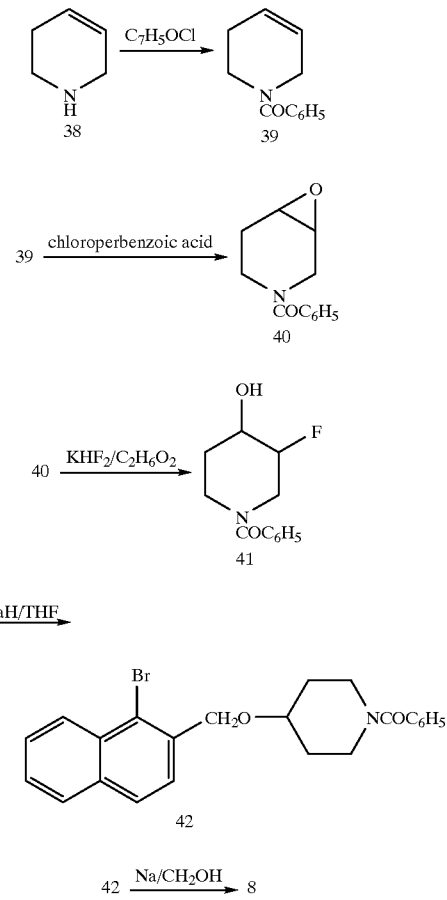

Scheme 9
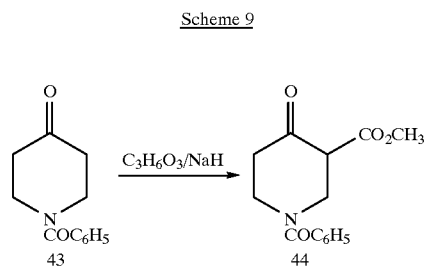
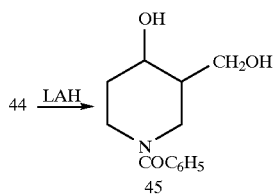
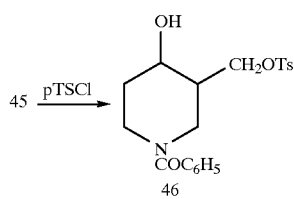
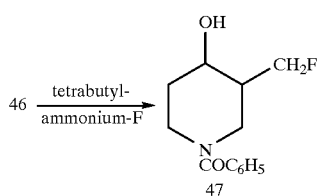
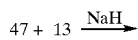 47 + 13 →(NaH)
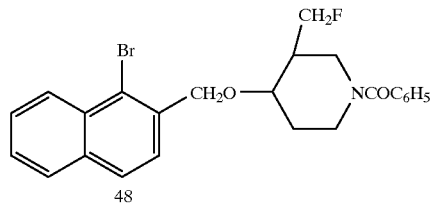
48 →(HCl/dioxane) 9
Scheme 10
43 →($C_4H_7BrO_2$) 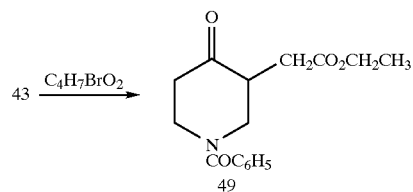
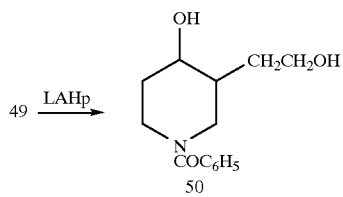
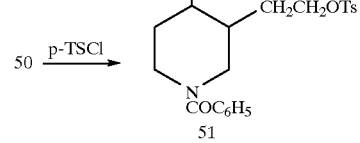
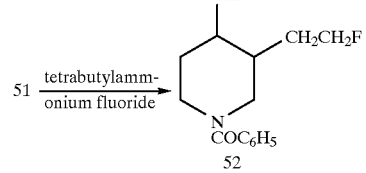
52 + 13 →(NaH/THF)
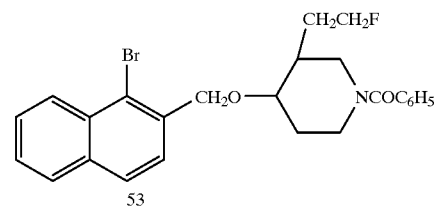
53 →(Na/$CH_3OH$) 10
Scheme 11
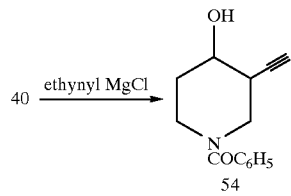
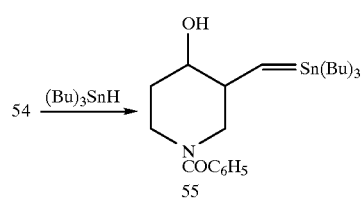

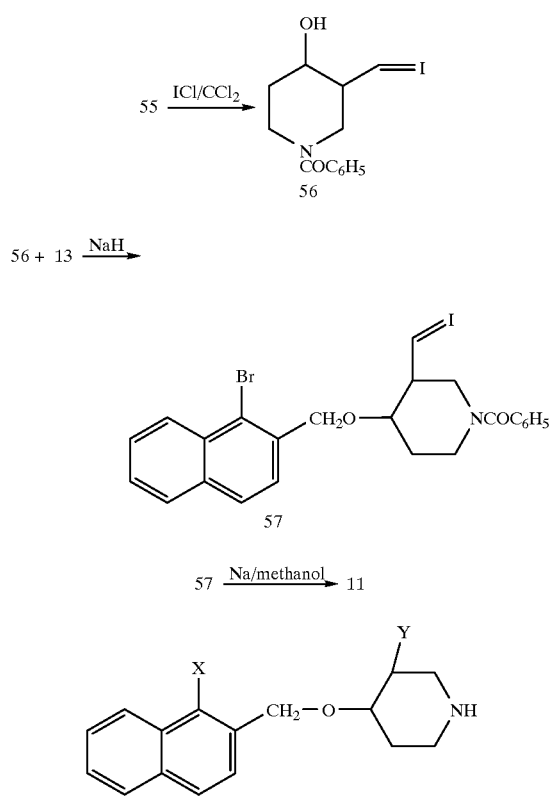
Scheme 12
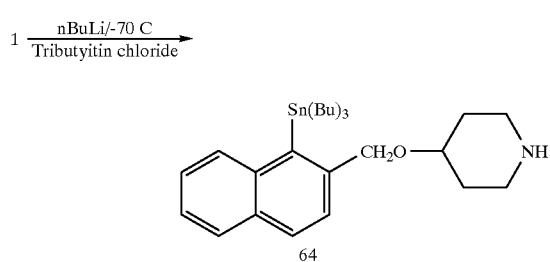
Scheme 13
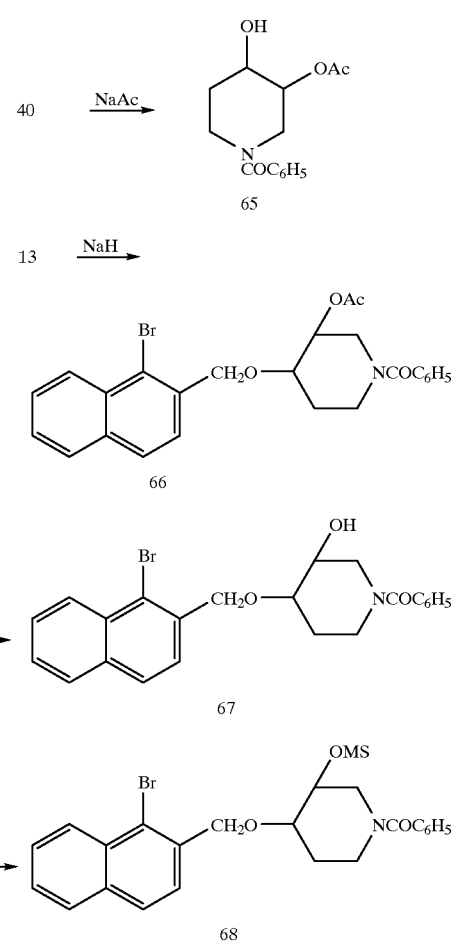
Scheme 14
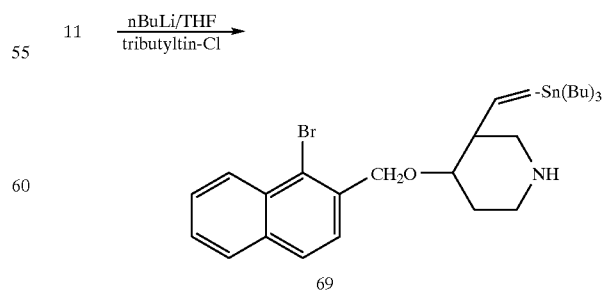

-continued

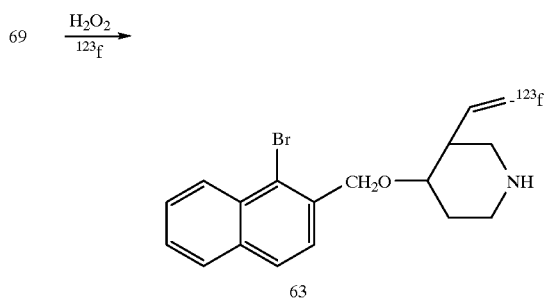

Scheme 15

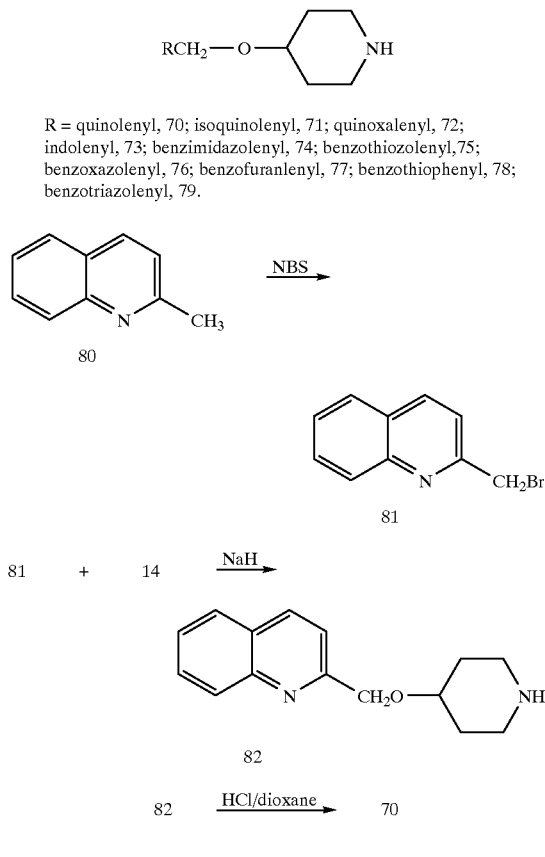

We claim:
1. A compound having the general structure

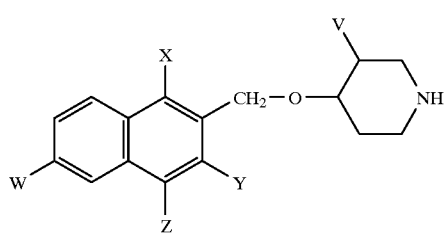

wherein W, X, Y and Z are independently H or halogen wherein at least one of W, X, Y or Z is a halogen and V is H, F, $^{18}$F, $(CH_2)_nF$, $(CH_2)_n{}^{18}F$, —CH——I, —CH=CH$^{123}$I or —CH=CH$^{125}$I, —CH=CHBr, —CH=CH$^{xy}$Br where xy is 75, 76, 77 or 82, and n is 0, 1 or 2.

2. The compound of claim 1 wherein X is halogen.

3. The compound of claim 1 wherein X is I, $^{123}$I, $^{125}$I, Br, $^{75}$Br, $^{76}$Br, $^{77}$Br, or $^{82}$Br.

4. The compound of claim 3 wherein Y is I, $^{123}$I or $^{125}$I.

5. The compound of claim 3 wherein Z is I, $^{123}$I or $^{125}$I.

6. The compound of claim 3 wherein W is I, $^{123}$I or $^{125}$I.

7. The compound of claim 1 wherein X is Br and V is $CH_2F$ or $CH_2{}^{18}F$.

8. The compound of claim 1 wherein V is $(CH_2)_2F$ or $(CH_2)_2{}^{18}F$.

9. The compound of claim 1 wherein V is F or $^{18}$F.

10. The compound of claim 1 wherein V is —CH=CHI, —CH=CH$^{123}$I, —CH=CH$^{125}$I, —CH=CHBr or CH—CH$^{xy}$Br.

11. A compound having the structure $$RCH_2-O-\underset{NH}{\bigcirc}$$

wherein R is quinolenyl, isoquinolenyl, quinoxalenyl, indolenyl, benzimidazolenyl, benzothiozolenyl, benzoxazolenyl, benzofuranlenyl, or benzotriazolenyl.

12. A method for positron emission tomography imaging comprising labeling serotonin transporter sites with an image-generating amount of a compound according to claim 1 having at least one halogen substituent selected from the group $^{18}$F, $^{75}$Br, $^{76}$Br, $^{77}$Br or $^{12}$Br and measuring spatial distribution of the compound by positron emission tomography.

13. A method for single photon emission spectroscopy imaging comprising labeling serotonin transporter sites with an image-generating amount of a compound according to claim 1 having at least one halogen substituent as $^{123}$I or $^{125}$I, and measuring spatial distribution of the compound by single photon emission spectroscopy.

14. A method for inhibiting 5-HT$_3$ receptor activity in vitro comprising contacting 5-HT$_3$ receptors in a tissue with an inhibiting amount of a compound according to claim 11.

15. A method of diagnosis or treatment of a psychiatric, psychomotor or addiction disorder selected from the group consisting of depression, obsessive-compulsive disorder, Parkinson's disease, Alzheimer's disease, and alcohol abuse by administering to a patient for whom diagnosis or treatment is indicated a 5-HT$_3$ receptor activity inhibiting amount of a compound according to claim 11.

* * * * *

UNITED STATES PATENT AND TRADEMARK OFFICE
CERTIFICATE OF CORRECTION

PATENT NO. : 5,919,797

DATED : July 6, 1999

INVENTOR(S) : Goodman et al.

It is certified that error appears in the above-identified patent and that said Letters Patent is hereby corrected as shown below:

At Col. 1, line 9, delete "+gi"

At Col. 3, line 36, "delete $^{125/l}$"  and replace with $--^{125}I--$

At Col. 16, Scheme 1,
delete compound 13 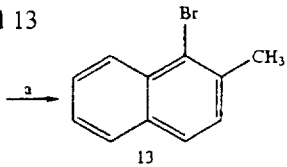  and replace with 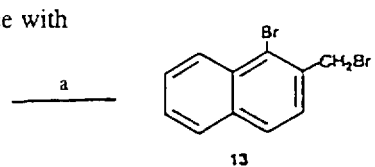

At Col. 16, Scheme 2,
delete compound 16 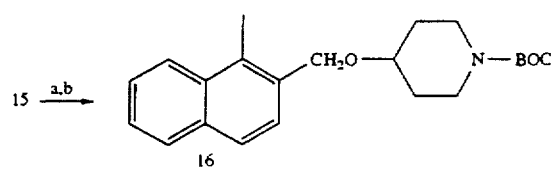  and replace with 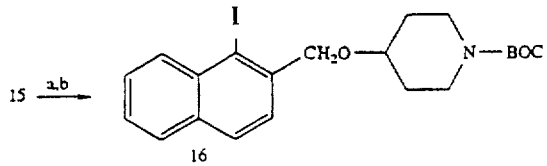

At Col. 20, Scheme 8,
delete compound 42 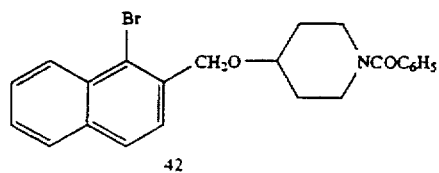  and replace with 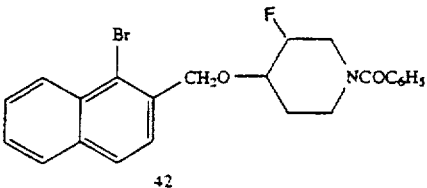

UNITED STATES PATENT AND TRADEMARK OFFICE
CERTIFICATE OF CORRECTION

PATENT NO. : 5,919,797

DATED : July 6, 1999

INVENTOR(S) : Goodman et al.

It is certified that error appears in the above-identified patent and that said Letters Patent is hereby corrected as shown below:

At Col. 23, Scheme 11, line 35,
delete "$-CH_2CH_2{}^{18}F$ 62" and replace with ---$CH_2{}^{18}F$ 61--

At Col. 23, Scheme 12,
delete the equation and replace with

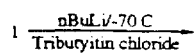
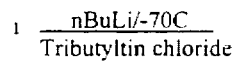

At Col. 25, Scheme 14,
delete the second part of compound 69 and replace with

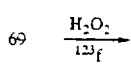
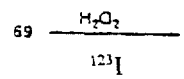

and delete compound 63 and replace with

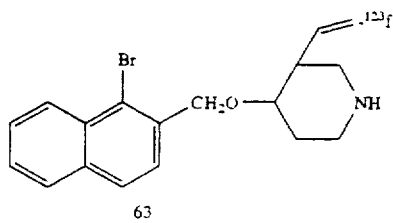
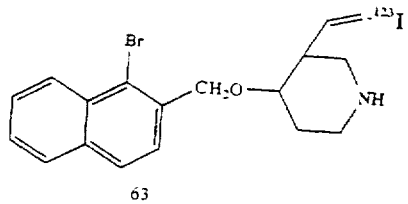

UNITED STATES PATENT AND TRADEMARK OFFICE
CERTIFICATE OF CORRECTION

PATENT NO. : 5,919,797

DATED : July 6, 1999

INVENTOR(S) : Goodman et al.

It is certified that error appears in the above-identified patent and that said Letters Patent is hereby corrected as shown below:

At Col. 4, line 13, delete "$^{18}F(CH_2)_n{}^{18}F$ and replace with --$^{18}F,(CH_2)_n{}^{18}F$--.

At Col. 4, line 13, delete "$CH=CHI-CH=CH^{123}I$," and replace with --$CH=CHI, CH=CH^{123}I$,--.

At Col. 4, line 14, delete "$-CH-CH^{125}I$," and replace with --$CH=CH^{125}I$,--; and delete "$-CH-CHBr$," and replace with --$CH=CHBr$,--.

At Col. 17, Scheme 3 between lines 5 and 10, delete "F-Dibebzene-sulfonamide" and replace with --F-Dibenzene-sulfonamide--.

In Claim 1, at Col. 26, line 3, delete "$-CH-I$," and replace with --$CH=CH-I$,--.

In Claim 10, at Col. 26, line 26, delete "$CH-CH^{xy}Br$." and replace with --$CH=CH^{xy}Br$.--.

UNITED STATES PATENT AND TRADEMARK OFFICE
CERTIFICATE OF CORRECTION

PATENT NO. : 5,919,797

DATED : July 6, 1999

INVENTOR(S) : Goodman et al.

It is certified that error appears in the above-identified patent and that said Letters Patent is hereby corrected as shown below:

In Claim 12, at Col. 26, line 44, delete "$^{12}$Br" and replace with --$^{82}$Br--

Signed and Sealed this

Fourteenth Day of December, 1999

Attest:

Attesting Officer

Q. TODD DICKINSON

Acting Commissioner of Patents and Trademarks